(12) United States Patent
Kesti-Helia et al.

(10) Patent No.: US 10,722,730 B2
(45) Date of Patent: Jul. 28, 2020

(54) SYSTEMS AND METHODS FOR GENERATING BEAM-SPECIFIC PLANNING TARGET VOLUME DESIGN OUTPUTS

(71) Applicant: Varian Medical Systems International AG

(72) Inventors: Anssi Kesti-Helia, Espoo (FI); Sampsa Lappalainen, Helsinki (FI); Timo K. Koponen, Helsinki (FI); Perttu Niemela, Espoo (FI)

(73) Assignee: Varian Medical Systems International AG, Cham (CH)

( * ) Notice: Subject to any disclaimer, the term of this patent is extended or adjusted under 35 U.S.C. 154(b) by 182 days.

(21) Appl. No.: 15/716,298

(22) Filed: Sep. 26, 2017

(65) Prior Publication Data

US 2018/0021595 A1    Jan. 25, 2018

Related U.S. Application Data

(63) Continuation of application No. 15/076,439, filed on Mar. 21, 2016, now Pat. No. 9,849,306.

(51) Int. Cl.
*A61N 5/10* (2006.01)
(52) U.S. Cl.
CPC ...... *A61N 5/103* (2013.01); *A61N 2005/1074* (2013.01)
(58) Field of Classification Search
None
See application file for complete search history.

(56) References Cited

U.S. PATENT DOCUMENTS

2002/0106054 A1    8/2002   Caflisch et al.
2005/0111621 A1    5/2005   Riker et al.
2007/0100233 A1*   5/2007   Thomson ............. A61N 5/1049
                                                   600/427

(Continued)

OTHER PUBLICATIONS

Park et al., "A Beam-Specific Planning Target Volume (PTV) Design for Proton Therapy to Account for Setup and Range Uncertainties," Published Jun. 22, 2011, Int J Radiat Oncol Biol Phys., Feb. 1, 2013, vol. 82, No. 2, pp. e329-e336. 10 pages.

*Primary Examiner* — Hoon K Song
(74) *Attorney, Agent, or Firm* — Duane Morris LLP; Manita Rawat

(57) ABSTRACT

System includes a beam generator to generate beam(s) for patient treatment and a computing device that obtains three-dimensional image(s) of a target structure that repositions with respect to surrounding tissue of the patient. The computing device creates plan(s) including a first three-dimensional probability distribution of patient's position and a second three-dimensional probability distribution of the repositioned structure's internal position. The computing device combines the first distribution with the second distribution to generate a joint distribution and selects a probability level from the joint distribution. The probability level defines an enclosed surface. A distance defined between the surface and a point of origin in at least one direction is equal to a threshold value of a parameter of the repositioned target in the direction. The computing device projects the surface to a plane positioned relative to a direction of the beam for the generation of beam-specific planning target volume design output(s).

20 Claims, 3 Drawing Sheets

(56) References Cited

U.S. PATENT DOCUMENTS

| | | | |
|---|---|---|---|
| 2010/0172469 A1* | 7/2010 | Poulsen | A61B 6/12 378/20 |
| 2014/0257012 A1 | 9/2014 | Hastenteufel et al. | |
| 2015/0062303 A1* | 3/2015 | Hanson | H04N 5/2252 348/47 |
| 2015/0174431 A1 | 6/2015 | Bharat | |

* cited by examiner

SYSTEMS AND METHODS FOR GENERATING BEAM-SPECIFIC PLANNING TARGET VOLUME DESIGN OUTPUTS

RELATED AND CO-PENDING APPLICATION

This application is a continuation of and claims priority to U.S. patent application Ser. No. 15/076,439 entitled SYSTEMS AND METHODS FOR GENERATING BEAM-SPECIFIC PLANNING TARGET VOLUME DESIGN OUTPUTS, filed on Mar. 21, 2016, the disclosure of which is incorporated herein by reference in its entirety.

BACKGROUND

In systems, such as radiation therapy systems, ionizing radiation techniques are used to treat various tissues, such as tumors. At least some known ionizing radiation techniques that are used in radiation therapy systems include electron beams, x-rays, and proton beams. These techniques enable a radiologist to treat patients from multiple angles, while also varying the shape and dose of the radiation beam. This approach also enables the delivery of radiation to a target within a treatment volume while avoiding excess irradiation of adjacent healthy tissue. In order to deliver radiation appropriately, treatment planning is used.

At least some known treatment planning methods consider various parameters, such as dosage of radiation being delivered, patient setup uncertainty, proton beam range parameters, and/or organ motion. For example, in photon treatment planning, at least some of these parameters are addressed by using geometrical concepts, such as planning target volume ("PTV"). In at least some know methods, the PTV is generated by including geometric margins to the clinical target volume ("CTV"). The CTV to PTV margins can be ascertained by considering uncertainties that can occur during the delivery of the treatment beam.

In proton planning, however, at least some known PTV designs are not able to provide a robust plan. This problem can occur more often for proton planning than photon planning, as protons deposit energy in a different way than photons. As such, patient setup error and internal target motion may have a significant impact on the coverage of a target structure, such as the tissue of a tumor, and the exposure of normal tissue. Moreover, the distal fall of the dose can be relatively sharp or steep. As such, there can be range uncertainty caused by, for example, calibration inaccuracies in the equipment used, such as a computerized tomography ("CT") scanner. All of these known issues may result in the treatment of more normal tissue that surrounds the target structure (i.e., tumor). Moreover, at least part of the target structure may not get treated. As a result, the target may be unable to obtain the full treatment dose,

BRIEF DESCRIPTION

The embodiments described herein enables less normal tissue from being treated by generating a beam-specific planning target volume ("PTV") design that takes into account the patient setup error, the internal target motion, and range uncertainty around the clinical target volume ("CTV"). For example, in some embodiments, a system is provided that includes a beam generator configured to generate at least one beam to treat a patient. At least one computing device is coupled to the beam generator, wherein the computing device is configured to obtain at least one three-dimensional image of a target structure and surrounding tissue of the patient, wherein the target structure is configured to move, be repositioned, and/or delineate with respect to the surrounding tissue. The computing device is also configured to create a treatment plan that includes at least one first three-dimensional probability distribution of a position of the patient and at least one second three-dimensional probability distribution of an internal position of the repositioned target structure. The computing device is configured to combine the first three-dimensional probability distribution with the second three-dimensional probability distribution to generate a joint distribution of the position of the patient and the internal position of the repositioned target structure. The computing device is also configured to select a probability level from the joint distribution such that the probability level defines an enclosed surface, wherein a distance defined between a portion of the enclosed surface and a point of origin in at least one direction is equal to or greater than a predefined threshold value of the repositioned target structure, such as a predefined worst-case scenario movement of the repositioned target structure in the direction. The computing device is further configured to project the enclosed surface to a plane that is positioned relative to a direction of the beam to facilitate the generation of at least one beam-specific planning target volume design output.

In other embodiments, a method is provided that includes coupling at least one computing device to a beam generator that is configured to generate at least one beam to treat a patient. At least one three-dimensional image of a target structure and surrounding tissue of the patient is obtained, wherein the target structure is configured to move, be repositioned, and/or delineate with respect to the surrounding tissue. A treatment plan that includes at least one first three-dimensional probability distribution of a position of the patient and at least one second three-dimensional probability distribution of an internal position of the repositioned target structure is created. The first three-dimensional probability distribution is combined with the second three-dimensional probability distribution to generate a joint distribution of the position of the patient and the internal position of repositioned target structure. A probability level is selected from the joint distribution such that the probability level defines an enclosed surface, wherein a distance defined between a portion of the enclosed surface and a point of origin in at least one direction is equal to or greater than a predefined threshold value of the repositioned target structure, such as a predefined worst-case scenario movement of the repositioned target structure in the direction. The method also includes projecting the enclosed surface to a plane that is positioned relative to a direction of the beam to facilitate the generation of at least one beam-specific planning target volume design output.

In yet other embodiments, at least one computer-readable storage medium having computer-executable instructions embodied thereon is provided, wherein, when executed by at least one processor, the computer-executable instructions cause the processor to obtain at least one three-dimensional image of a target structure and surrounding tissue of a patient, wherein the target structure is configured to move, be repositioned, and/or delineate with respect to the surrounding tissue. The computer-executable instructions also cause the processor to create a treatment plan that includes at least one first three-dimensional probability distribution of a position of the patient and at least one second three-dimensional probability distribution of an internal position of the repositioned target structure. The computer-executable instructions further cause the processor to combine the first three-dimensional probability distribution with the second three-dimensional probability distribution to generate a joint distribution of the position of the patient and the internal position of the repositioned target structure. Moreover, the computer-executable instructions cause the processor to select a probability level from the joint distribution such that the probability level defines an enclosed surface, wherein a distance defined between a portion of the enclosed surface and a point of origin in at least one direction is equal to or greater than a predefined threshold value of the repositioned target structure, such as a predefined worst-case scenario movement of the repositioned target structure in the direction and to project the enclosed surface to a plane that is positioned relative to a direction of at least one beam to facilitate the generation of at least one beam-specific planning target volume design output.

DETAILED DESCRIPTION

Figure 1:
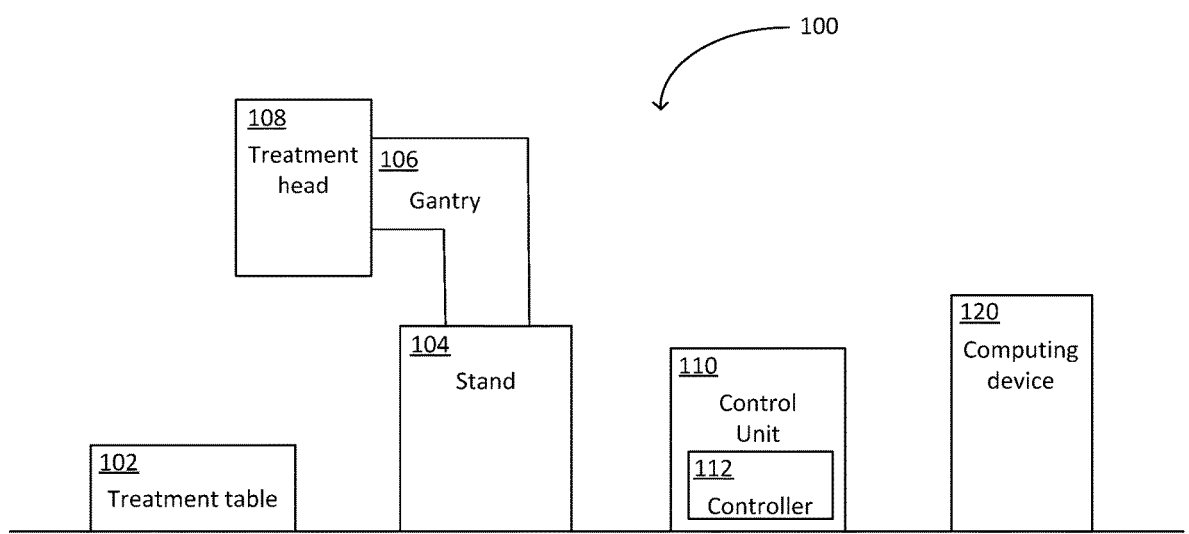
FIG. 1 is a block diagram of an exemplary system.

The following disclosure provides many different embodiments, or examples, for implementing different features of the subject matter. Specific examples of components and arrangements are described below to simplify the present disclosure. These are, of course, merely examples and are not intended to be limiting. For example, the formation of a first feature over or on a second feature in the description that follows may include embodiments in which the first and second features are formed in direct contact, and may also include embodiments in which additional features may be formed between the first and second features, such that the first and second features may not be in direct contact. In addition, the present disclosure may repeat reference numerals and/or letters in the various examples. This repetition is for the purpose of simplicity and clarity and does not in itself dictate a relationship between the various embodiments and/or configurations discussed.

In describing the various embodiments herein, "radiation" refers to any particles (e.g., photons, electrons, protons etc.) used to treat tissue, e.g., tumors. Examples of radiation include high energy x-rays, gamma rays, electron beams, and proton beams. The different particles can correspond to different types of radiation treatments. The "treatment volume" refers to the entire volume that will be subjected to radiation, and is sometimes referred to as the "irradiated volume." The "target structure", "target volume", and "planning target volume" ("PTV") refer to tissue intended to receive a therapeutic prescribed dose. A "treatment plan" can include workflow outputs and/or reports with a dose distribution and/or machine parameters for achieving the dose distribution for a given patient, and information about the given patient. A dose distribution provides information about the variation in the dose of radiation with position. A "dose distribution" can take many forms, e.g., a dose volume histogram ("DVH") or a dose matrix.

It should also be noted that, as used herein, the term "couple" is not limited to a direct mechanical and/or an electrical connection between components, but may also include an indirect mechanical and/or electrical connection between two or more components or a coupling that is operative through intermediate elements or spaces.

As described above, in proton planning, the PTV is unable to be robustly defined, as protons deposit energy in a very different way than photons and there can be range uncertainty caused by, for example, calibration inaccuracies in the equipment used, such as a computerized tomography ("CT") scanner. As a result, treatment of more normal tissue that surrounds the target structure (i.e., tumor) can occur. The embodiments described herein enables less normal tissue from being treated by using a beam-specific PTV design that takes into account the patient setup error, the internal target motion, and range uncertainty around the clinical target volume ("CTV").

FIG. 1 illustrates a block diagram of an exemplary system 100, such as a radiation therapy system, that is configured to treat affected tissue, such as cancer tissue, on a patient. In some embodiments, system 100 includes a treatment table 102 that a patient can be positioned on. System 100 can also include a stand 104, which supports a rotatable gantry 106 with a beam generator or treatment head 108. In some embodiments, treatment head 108 is configured to generate an electron (particle) beam or an x-ray (photon) beam for use in the radiation therapy or radiotherapy treatment of patients on treatment table 102. In some embodiments, treatment head 108 is configured to generate heavy ion particles, such as protons.

A control unit 110 is positioned next to stand 104, wherein control unit 110 includes a controller 112 that is configured for controlling the different modes of operation of an accelerator (not shown). For example, controller 112 can be configured to facilitate operative features of various components of the accelerator, via features that include, without limitation, receiving inputs and/or transmitting outputs. In some embodiments, controller 112 can be a real-time controller and can include any suitable processor-based or microprocessor-based system, such as a computer system, that includes microcontrollers, reduced instruction set computer ("RISC"), an embedded microprocessor, application-specific integrated circuits ("ASICs"), logic circuits, and/or any other circuit or processor that is capable of executing the functions described herein. In some embodiments, controller 112 can be a microprocessor that includes read-only memory ("ROM") and/or random access memory ("RAM"). As used herein, the term "real-time" refers to outcomes occurring within a short period of time after a change in the inputs affect the outcome, with the time period being a design parameter that can be selected based on the importance of the outcome and/or the capability of the system processing the inputs to generate the outcome.

In some embodiments, system 100 also includes a user computing device 120 that can be coupled to controller 112. Computing device 120 can be a desktop computer, laptop, mobile device, tablet, thin client, or other suitable device that enables system 100 to function as described herein.

Figure 2:
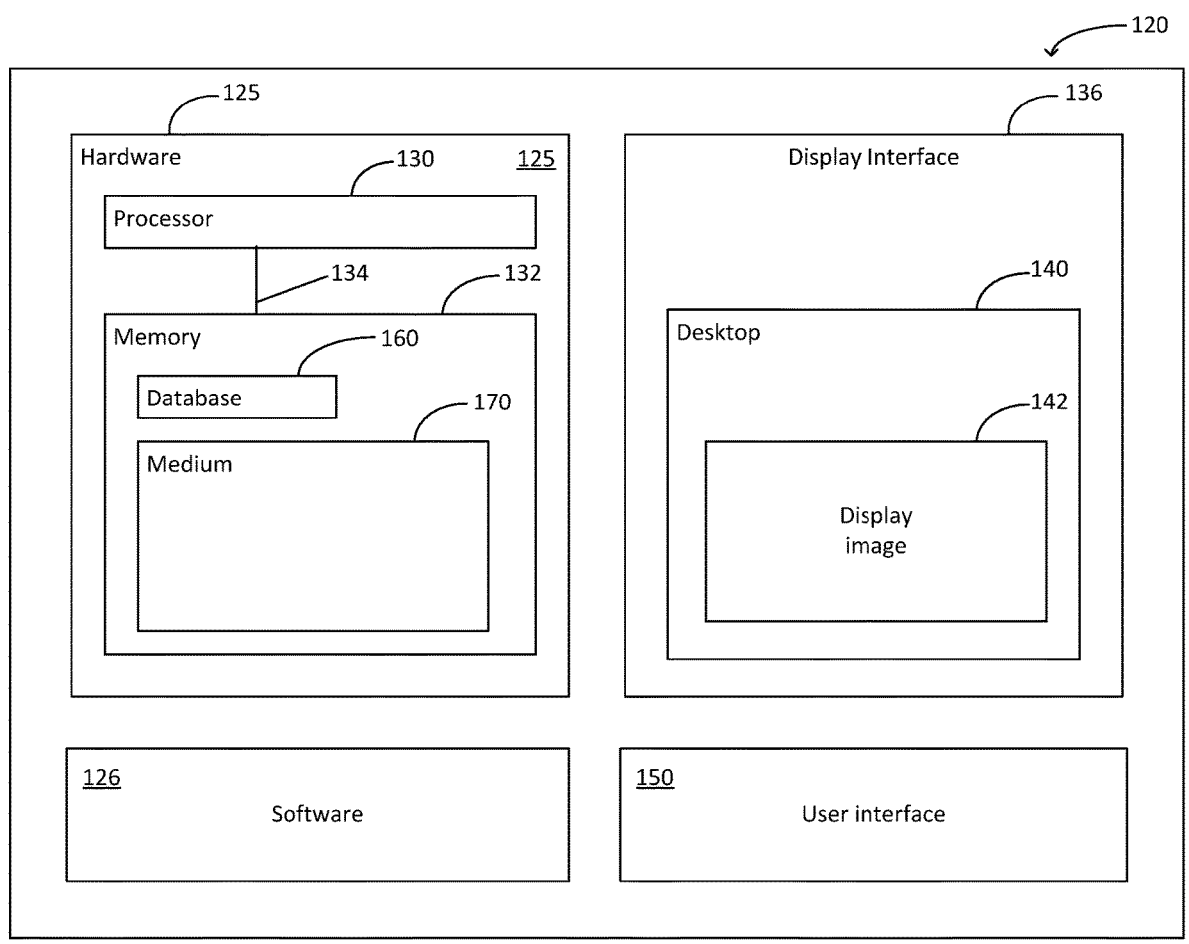
FIG. 2 is a block diagram of exemplary computing device that can be used with the system shown in FIG. 1.

FIG. 2 illustrates a block diagram of computing device 120. In some embodiments, computing device 120 includes a hardware unit 125 and software 126. Software 126 can run on hardware unit 125 such that various applications or programs can be executed on hardware unit 125 by way of software 126. In some embodiments, the functions of software 126 can be implemented directly in hardware unit 125, e.g., as a system-on-a-chip, firmware, field-programmable gate array ("FPGA"), etc. In some embodiments, hardware unit 125 includes one or more processors, such as processor 130. In some embodiments, processor 130 is an execution unit, or "core," on a microprocessor chip. In some embodiments, processor 130 may include a processing unit, such as, without limitation, an integrated circuit ("IC"), an ASIC, a microcomputer, a programmable logic controller ("PLC"), and/or any other programmable circuit. Alternatively, processor 130 may include multiple processing units (e.g., in a multi-core configuration). The above examples are exemplary only, and, thus, are not intended to limit in any way the definition and/or meaning of the term "processor."

Hardware unit 125 also includes a system memory 132 that is coupled to processor 130 via a system bus 134. Memory 132 can be a general volatile RAM. For example, in some embodiments, hardware unit 125 can include a 32 bit microcomputer with 2 Mbit ROM and 64 Kbit RAM. Memory 132 can also be a ROM, a network interface (NIC), and/or other device(s).

In some embodiments, computing device 120 can also include at least one media output component or display interface 136 for use in presenting information to a user. Display interface 136 can be any component capable of conveying information to a user and may include, without limitation, a display device (not shown) (e.g., a liquid crystal display ("LCD"), an organic light emitting diode ("OLED") display, or an audio output device (e.g., a speaker or headphones)). In some embodiments, computing device 120 can output at least one desktop, such as desktop 140. Desktop 140 can be an interactive user environment provided by an operating system and/or applications running within computing device 120, and can include at least one screen or display image, such as display image 142. Desktop 140 can also accept input from a user in the form of device inputs, such as keyboard and mouse inputs. In some embodiments, desktop 140 can also accept simulated inputs, such as simulated keyboard and mouse inputs. In addition to user input and/or output, desktop 140 can send and receive device data, such as input and/or output for a FLASH memory device local to the user, or to a local printer.

In some embodiments, display image 142 can be presented to a user on computer displays of a remote terminal (not shown). For example, computing device 120 can be connected to one or more remote terminals (not shown) or servers (not shown) via a network (not shown), wherein the network can be the Internet, a local area network ("LAN"), a wide area network ("WAN"), a personal area network ("PAN"), or any combination thereof, and the network can transmit information between computing device 120 and the remote terminals or the servers, such that remote end users can access the information from computing device 120.

In some embodiments, computing device 120 includes an input or a user interface 150 for receiving input from a user. User interface 150 may include, for example, a keyboard, a pointing device, a mouse, a stylus, a touch sensitive panel (e.g., a touch pad or a touch screen), a gyroscope, an accelerometer, a position detector, and/or an audio input device. A single component, such as a touch screen, may function as both an output device of the media output component and the input interface. In some embodiments, mobile devices, such as tablets, can be used.

Computing device 120, in some embodiments, can include a database 160 within memory 132, such that various information can be stored within database 160. Alternatively, in some embodiments, database 160 can be included within a remote server (not shown) with file sharing capabilities, such that database 160 can be accessed by computing device 120 and/or remote end users. In some embodiments, a plurality of computer-executable instructions can be stored in memory 132, such as one or more computer-readable storage mediums 170 (only one being shown in FIG. 2). Computer storage medium 170 includes non-transitory media and may include volatile and nonvolatile, removable and non-removable mediums implemented in any method or technology for storage of information such as computer-readable instructions, data structures, program modules or other data. The instructions may be executed by processor 130 to perform the functions described in more detail below.

Figure 3:
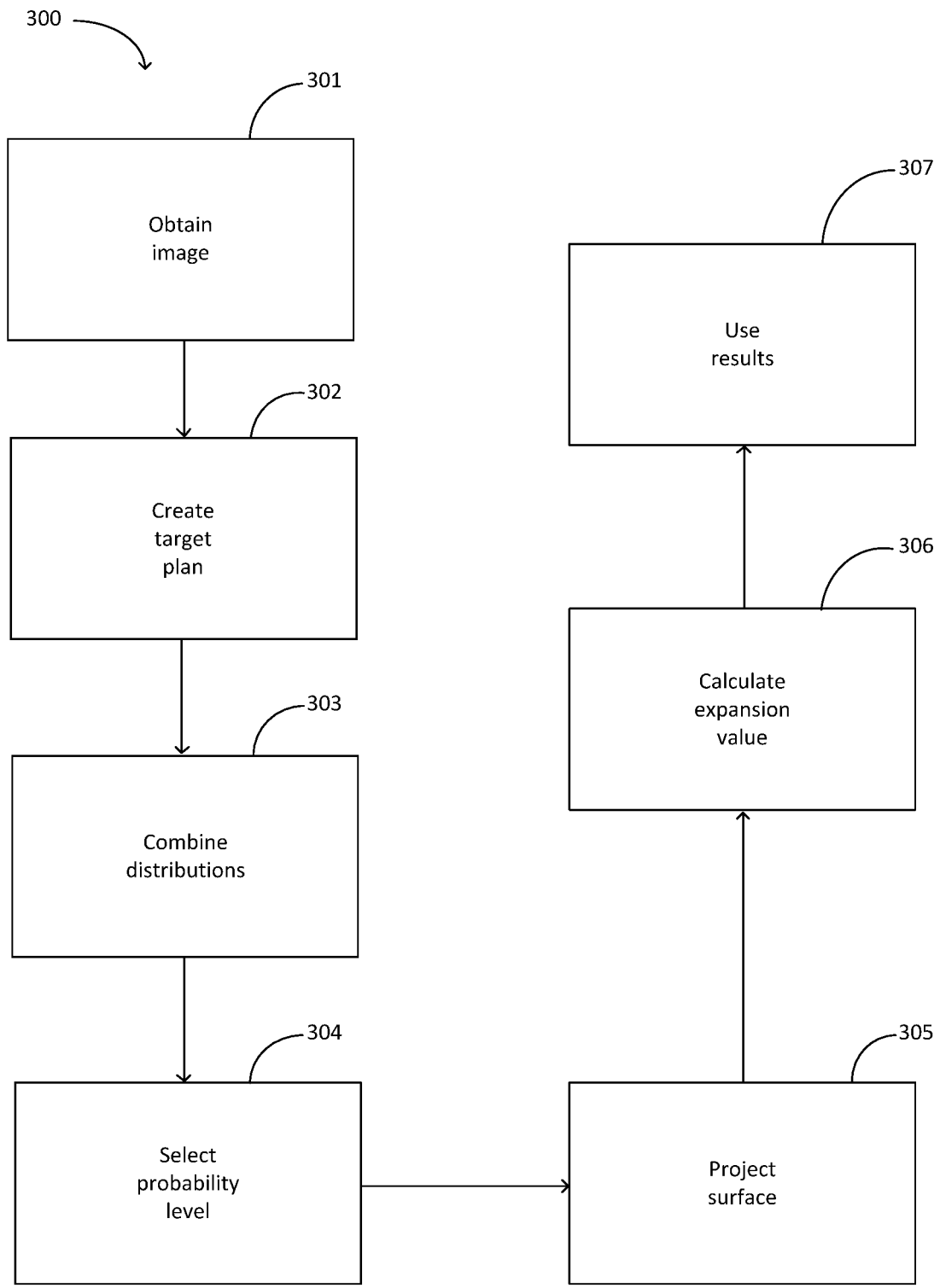
FIG. 3 is a flow diagram of an exemplary method for generating at least one beam-specific planning target volume design using the computing device shown in FIG. 2.

As explained in more detail with respect to FIG. 3, during operation of system 100 (shown in FIG. 1) and computing device 120, a user is enabled to generate a beam-specific PTV design output that takes into account the patient setup error, the internal target motion, and range uncertainty around the CTV for the radiation therapy treatment of a patient by system 100.

FIG. 3 is a flow diagram 300 of an exemplary method for generating at least one workflow output using a computing device, such as computing device 120 (shown in FIGS. 1 and 2). This method may be embodied within a plurality of computer-executable instructions stored in one or more memories, such as one or more computer-readable storage medium 170 (shown in FIG. 2). As described above, computer storage mediums 170 can include non-transitory media and may include volatile and nonvolatile, removable and non-removable mediums implemented in any method or technology for storage of information such as computer-readable instructions, data structures, program modules or other data. The instructions may be executed by one or more processors, such as processor 130 (shown in FIG. 2), to perform the functions described herein.

In step 301, at least one three-dimensional image of a target structure, such as a tumor, along with surrounding tissue, of a patient is obtained. In some embodiments, the image can be obtained using one or more imaging devices (not shown), such as a camera, that can be part of computing device 120 or a separate device coupled to computing device 120 and controlled by controller 112. The target structure, in some embodiments will move, change positions, or delineate. For example, the target structure may change positions with respect to the surrounding tissue. In step 302, a treatment plan is created. In some embodiments, the treatment plan includes at least one first three-dimensional probability distribution of a position of the patient and at least one second three-dimensional probability distribution of an internal position of the repositioned target structure. In some embodiments, for example, each of the distributions can be three-dimensional Gaussian distributions with known variances in x, y, and z directions in the patient geometry. Alternatively, in some embodiments, separate variances may be known and used for positive and negative x, y, and z directions, which can lead to a segmented defined three-dimensional Gaussian distribution. In some embodiments, the distributions can also be non-Gaussian. For example, the internal motion of organ can be shown in more complex distributions.

In some embodiments, when creating the treatment plan in step 302, a user can define values separately in each field (for each structure). The values that can be defined on a field level tool, such as, for example, base structure, setup error, internal target motion, smearing margins, calibration curve error percentage, and/or additional axial margins. In some embodiments, at least some of these values need to be filled in before a beam-specific PTV can be created. In some embodiments, the user can also copy plan level defaults as the beam-specific PTV generation values for each of the following value sets: setup error, internal target motion, smearing margins, and calibration curve error percentage and additional axial margins. In some embodiments, the plan level defaults are empty or partially empty, and copying from them will set the values as the same as what the user sees in a default value dialog, via a display interface, such as display interface 136 (shown in FIG. 2).

In step 303, the first three-dimensional probability distribution is combined with the second three-dimensional probability distribution to generate a joint distribution of the position of the patient and the internal position of the repositioned target structure. In step 304, a probability level is selected from the joint distribution such that the probability level is defined by an enclosed surface. In some embodiments, a distance defined between a portion or point on the surface and a point of origin in any direction is equal to or greater than a predefined threshold value of the repositioned target structure, such as a predefined worst-case scenario movement value of the repositioned target structure in the direction.

In step 305, the enclosed surface is projected to a plane, such as a two-dimensional ("2D") plane of voxels that are at a certain depth within the target volume, that is positioned relative to a direction of the beam to facilitate the generation of beam-specific PTV design output. In some embodiments, the plane is substantially perpendicular to the direction of the beam. In projecting the enclosed surface in step 305, computing device 120 identifies a volume enclosed by the predefined threshold value of the repositioned target structure, such as the predefined worst-case scenario movement of the repositioned target structure in the direction and discretizes the identified volume to a set of three-dimensional voxels. A two-dimensional matrix that includes a plurality of pixels is initialized and a plurality of lines are created such that each of the lines corresponds to a different pixel and such that each of the lines is parallel to the direction of the beam and intersects a center portion of each corresponding pixel.

In step 306, computing device 120 calculates an axial expansion value of the target structure and, in step 307, the results of the calculated axial expansion value are used to facilitate the generation of the beam-specific target volume design output. In some embodiments, the axial expansion value is used by at least one three-dimensional matrix. In some embodiments, in step 306, computing device 120 also calculates a lateral expansion value of the target structure, and the results of the calculation can also be used facilitate the generation of the beam-specific target volume design output in step 307. In some embodiments, the calculation of the lateral expansion value is based on at least one setup error value and internal target motion.

In some embodiments, when performing steps 301 to 307, setup error and internal target motion can be used for lateral expansion and smearing (lateral smoothing) and calibration curve error percentage and additional axial margins are used for axial expansion. Setup error can have no effect in the axial direction, because the water-equivalent value ("WED") may not change. Scattering can be different, but this effect can be negligible. Conceptually, internal target motion can be considered to have an effect also in the axial direction.

In some embodiments, the setup error and the target motion in patient geometry (patient X, Y, and Z) are to be defined. In performing these calculations, the algorithm being used may use margins in two separate steps. The first is the application of lateral margins to expand the structure. The second is smearing (lateral smoothing). The lateral expansion and smearing function is in two-dimensional lateral field geometry. As such, the setup error and internal target motion that are defined in three-dimensional patient geometry need to be projected to the two-dimensional lateral field geometry. Setup error and internal target motion are considered independent but equivalent sources of error. They are combined, in some embodiments, by calculating their Euclidean norm (square root of the quadratic sum). This sum is then projected to the two-dimensional lateral field geometry, yielding a two-dimensional margin kernel.

This two-dimensional projection is used in the lateral margin expansion step. In some embodiments, a user can use the same values in the lateral expansion step and the smearing step of the algorithm. In some embodiments, the user can use different values. For example, in some embodiments, the setup error and internal target motion parameters can be considered to form a volume of ellipsoid octants in the general case (because all the six directions right, left, anterior, posterior, feet, head can be different). When this volume of ellipsoid octants is projected to two-dimensional lateral field geometry, it becomes an "arbitrary" two-dimensional shape, which is represented by a two-dimensional segment, such as a kernel. In some embodiments, the kernel is first used for the lateral expansion. When the WED values are calculated to the two-dimensional matrix pixels, a ray is traced for each matrix pixel from the source to the base structure proximal and distal edges.

In some embodiments, the conversion can work by starting with an empty structure and looping through each voxel in the structure. The structure voxel can be transformed to beam geometry, wherein the two-dimensional matrix has an X/Y position and X/Y size in beam geometry, and wherein the position is the center of the matrix. The structure voxel is transformed from beam geometry to target matrix geometry. This also projects the three-dimensional structure voxel to the two-dimensional matrix plane. This step can take the beam divergence into account. The resolution of the structure and the resolution of the two-dimensional matrix can be different. Also, the orientation of the matrix (i.e. the beam) can be different from the orientation of the structure (patient image) in the general case. Thus, the pixels/voxels of the matrix and the structure do not coincide.

In some embodiments, the distance of both matrices is calculated as described above. This distance is the z value of the matrix in the beam geometry. The user also has the z value of the structure voxel in the beam geometry from the earlier transformation. In some embodiments, the user can then compare the z values and determine whether the structure voxel is between the matrices or not. The user is enabled to know whether the structure voxel should be inside or outside the resulting structure. Values for the voxels close to the edge can be calculated separately.

In some embodiments, setup error and internal target motion can be defined in patient geometry in three dimensions. For example, computing device 120 can calculate the square root of the quadratic sum of the setup error and the internal target motion. For example, if setup error is 0.3 and internal target motion is 0.4, the result is $\sqrt{0.3^2+0.4^2}=0.5$. This calculation can be done separately for each input direction. Alternatively, in some embodiments, a user can implement the algorithm by defining one set of values.

In some embodiments, when considering the margin expansions, the target, based on the base structure, is expanded laterally (with regards to the field; X and Y) with the two-dimensional projection (of the combined setup error and internal target motion values). The field-specific target is calculated into two two-dimensional matrices; a proximal matrix and a distal matrix. Computing device 120 can calculate the WED value for each individual ray from the source to the proximal and distal matrices (represented by a pixel in each matrix).

In some embodiments, smearing is performed on the WED values of the pixels in the matrices in two dimensions (X and Y). The calibration curve error percentage is added to the WED values of the pixels in the matrices. The WED values of the pixels in the matrices are converted back to geometric distances. The additional proximal and distal margins are added to the geometric distance values of the pixels in the matrices. The two two-dimensional matrices can define the proximal and distal edges of the beam-specific target. Computing device 120 can connect the lateral edges of the two-dimensional matrices to create a closed three-dimensional volume. In some embodiments, if the three-dimensional volume extends beyond the body, the parts outside the body are removed. In some embodiments, Gaussian smoothing (i.e., two-dimensional-convolution with a Gaussian kernel) is performed on the (Z slice) contours of the three-dimensional volume.

Exemplary embodiments of systems and methods are described above in detail. The systems and methods are not limited to the specific embodiments described herein, but rather, components of each system and/or method may be utilized independently and separately from other components described herein. For example, each system may also be used in combination with other systems and is not limited to practice with only systems as described herein. Rather, the exemplary embodiment can be implemented and utilized in connection with many other applications.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and also to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A system comprising at least one computing device configured to:
   identify a position of a patient, wherein a target structure is located on the patient and the target structure is at least partially surrounded by tissue of the patient, the target structure being configured to move from a first position to a second position with respect to the surrounding tissue, the second position being different from the first position;
   generate at least one first output that is representative of the position of the patient, wherein the at least one first output is at least one first three-dimensional probability distribution of the position of the patient;
   obtain data of the target structure and the surrounding tissue of the patient when the target structure has moved from the first position to the second position;
   generate at least one second output of the target structure based, at least in part, on the obtained data, wherein the at least one second output is at least one second three-dimensional probability distribution of an internal position of the target structure having moved from the first position to the second position;
   combine the at least one first three-dimensional probability distribution with the at least one second three-dimensional probability distribution to generate a joint distribution of the position of the patient and the internal position of the target structure in the second position; and
   generate at least one beam-specific planning target volume design output based at least on the joint distribution.

2. A system in accordance with claim 1, wherein the obtained data includes at least one image of the target structure and the surrounding tissue of the patient.

3. A system in accordance with claim 2, wherein the at least one image is at least one three-dimensional image.

4. A system in accordance with claim 1, wherein said at least one computing device is further configured to select a probability level from the joint distribution such that the probability level defines an enclosed surface.

5. A system in accordance with claim 1, wherein said at least one computing device is further configured to create a treatment plan that includes the at least one first output and the at least one second output.

6. A method of generating at least one beam-specific planning target volume design output, said method comprising:
   identifying a position of a patient, wherein a target structure is located on the patient and the target structure is at least partially surrounded by tissue of the patient, the target structure being configured to move from a first position to a second position with respect to the surrounding tissue, the second position being different from the first position;
   generating at least one first output that is representative of the position of the patient, wherein the at least one first output is at least one first three-dimensional probability distribution of the position of the patient;
   obtaining data of the target structure and the surrounding tissue of the patient when the target structure has moved from the first position to the second position;
   generating at least one second output of the target structure based, at least in part, on the obtained data, wherein the at least one second output is at least one second three-dimensional probability distribution of an internal position of the target structure having moved from the first position to the second position;
   combining the at least one first three-dimensional probability distribution with the at least one second three-dimensional probability distribution to generate a joint distribution of the position of the patient and the internal position of the target structure in the second position; and
   generating at least one beam-specific planning target volume design output based at least on the joint distribution.

7. A method in accordance with claim 6, wherein the obtained data includes at least one image of the target structure and the surrounding tissue of the patient.

8. A method in accordance with claim 7, wherein the at least one image is at least one three-dimensional image.

9. A method in accordance with claim 1, further comprising selecting a probability level from the joint distribution such that the probability level defines an enclosed surface.

10. A method in accordance with claim 6, further comprising creating a treatment plan that includes the at least one first output and the at least one second output.

11. At least one non-transitory computer-readable storage medium having computer-executable instructions embodied thereon, wherein, when executed by at least one processor, the computer-executable instructions cause the at least one processor to:
identify a position of a patient, wherein a target structure is located on the patient and the target structure is at least partially surrounded by tissue of the patient, the target structure being configured to move from a first position to a second position with respect to the surrounding tissue, the second position being different from the first position;
generate at least one first output that is representative of the position of the patient, wherein the at least one first output is at least one first three-dimensional probability distribution of the position of the patient;
obtain data of the target structure and the surrounding tissue of the patient when the target structure has moved from the first position to the second position;
generate at least one second output of the target structure based, at least in part, on the obtained data, wherein the at least one second output is at least one second three-dimensional probability distribution of an internal position of the target structure having moved from the first position to the second position;
combine the at least one first three-dimensional probability distribution with the at least one second three-dimensional probability distribution to generate a joint distribution of the position of the patient and the internal position of the target structure in the second position; and
generate at least one beam-specific planning target volume design output based at least on the joint distribution.

12. At least one non-transitory computer-readable storage medium in accordance with claim 11, wherein the obtained data includes at least one image of the target structure and the surrounding tissue of the patient.

13. At least one non-transitory computer-readable storage medium in accordance with claim 12, wherein the at least one image is at least one three-dimensional image.

14. At least one non-transitory computer-readable storage medium in accordance with claim 11, wherein the computer-executable instructions cause the at least one processor to select a probability level from the joint distribution such that the probability level defines an enclosed surface.

15. A system in accordance with claim 1, wherein said at least one computing device is further configured to obtain a setup error, wherein generating the at least one beam-specific planning target volume design output is based on the setup error.

16. A system in accordance with claim 1, wherein said at least one computing device is further configured to obtain an internal target motion of the target structure, wherein generating the at least one beam-specific planning target volume design output is based on the internal target motion.

17. A method in accordance with claim 6, further comprising obtaining a setup error, wherein generating the at least one beam-specific planning target volume design output is based on the setup error.

18. A method in accordance with claim 6, further comprising obtaining an internal target motion of the target structure, wherein generating the at least one beam-specific planning target volume design output is based on the internal target motion.

19. At least one non-transitory computer-readable storage medium in accordance with claim 11, wherein, when executed by the at least one processor, the computer-executable instructions further cause the at least one processor to obtain a setup error, wherein generating the at least one beam-specific planning target volume design output is based on the setup error.

20. At least one non-transitory computer-readable storage medium in accordance with claim 11, wherein, when executed by the at least one processor, the computer-executable instructions further cause the at least one processor to obtain an internal target motion of the target structure, wherein generating the at least one beam-specific planning target volume design output is based on the internal target motion.

* * * * *